US009332960B2

(12) United States Patent
Iddan

(10) Patent No.: US 9,332,960 B2
(45) Date of Patent: May 10, 2016

(54) SYSTEM AND METHOD FOR DETERMINING LOCATION AND ORIENTATION OF A DEVICE IN-VIVO

(75) Inventor: Gavriel J. Iddan, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 409 days.

(21) Appl. No.: 13/982,816

(22) PCT Filed: Feb. 1, 2012

(86) PCT No.: PCT/IB2012/000953
§ 371 (c)(1),
(2), (4) Date: Jul. 31, 2013

(87) PCT Pub. No.: WO2012/104733
PCT Pub. Date: Aug. 9, 2012

(65) Prior Publication Data
US 2013/0317357 A1    Nov. 28, 2013

Related U.S. Application Data

(60) Provisional application No. 61/439,197, filed on Feb. 3, 2011.

(51) Int. Cl.
*A61B 5/05* (2006.01)
*A61B 8/08* (2006.01)
(Continued)

(52) U.S. Cl.
CPC ........... *A61B 8/0841* (2013.01); *A61B 1/00158* (2013.01); *A61B 1/041* (2013.01);
(Continued)

(58) Field of Classification Search
None
See application file for complete search history.

(56) References Cited

U.S. PATENT DOCUMENTS

2003/0114742 A1*  6/2003  Lewkowicz ........ A61B 1/00147
                                                              600/407
2004/0204645 A1   10/2004  Saadat
                         (Continued)

FOREIGN PATENT DOCUMENTS

WO        WO 03/028224        4/2003

OTHER PUBLICATIONS

Kunin, Vitaliy, "Sound and Ultrasound Source Detection of Arrivial Estimation and Localization", Illinois Inst. Tech., Dec. 2010.*
International Search Report for International Application No. PCT/IB2012/000953 mailed Nov. 5, 2012.

*Primary Examiner* — Christopher Cook
(74) *Attorney, Agent, or Firm* — Pearl Cohen Zedek Latzer Baratz LLP

(57) ABSTRACT

A system and method for determining location and orientation of an in-vivo device, with respect to an external system in which the device is located include a frame with external magnets attached thereon. An in-vivo device is inserted into the patient's body, which is placed within the system, and the external magnets apply magnetic forces on the in-vivo device. A radio beacon transmitter is attached to the frame for transmitting a radio pulse. The in-vivo device includes an ultrasonic transmitter for transmitting an ultrasonic signal, which is triggered by the radio pulse. At least three transponders are placed on the patient's body, each transponder sending a first acoustic signal triggered by the radio pulse, and each sending a second acoustic signal triggered by the device's ultrasonic signal. At least three sonic detectors are located on the frame for detecting each of the transponders' first and second sonic signals, and a processor measures time of detection of the transponders' signals and thus calculates location of the device in frame coordinates, and in body coordinates.

10 Claims, 13 Drawing Sheets

(51) Int. Cl.
*A61B 1/00* (2006.01)
*A61B 1/04* (2006.01)
*A61B 5/06* (2006.01)
*A61B 5/07* (2006.01)
*A61B 8/00* (2006.01)
*A61B 17/00* (2006.01)

(52) U.S. Cl.
CPC ................ *A61B 5/065* (2013.01); *A61B 5/073* (2013.01); *A61B 8/52* (2013.01); *A61B 8/54* (2013.01); *A61B 17/00234* (2013.01)

(56) References Cited

U.S. PATENT DOCUMENTS

| | | | |
|---|---|---|---|
| 2008/0172119 A1* | 7/2008 | Yamasaki | A61B 5/06 623/1.11 |
| 2008/0275481 A1 | 11/2008 | Scarpone | |
| 2009/0105597 A1 | 4/2009 | Abraham | |
| 2011/0160129 A1* | 6/2011 | Imran | A61K 31/155 514/5.9 |
| 2012/0313790 A1* | 12/2012 | Heijnen | E21B 4/18 340/854.6 |

* cited by examiner

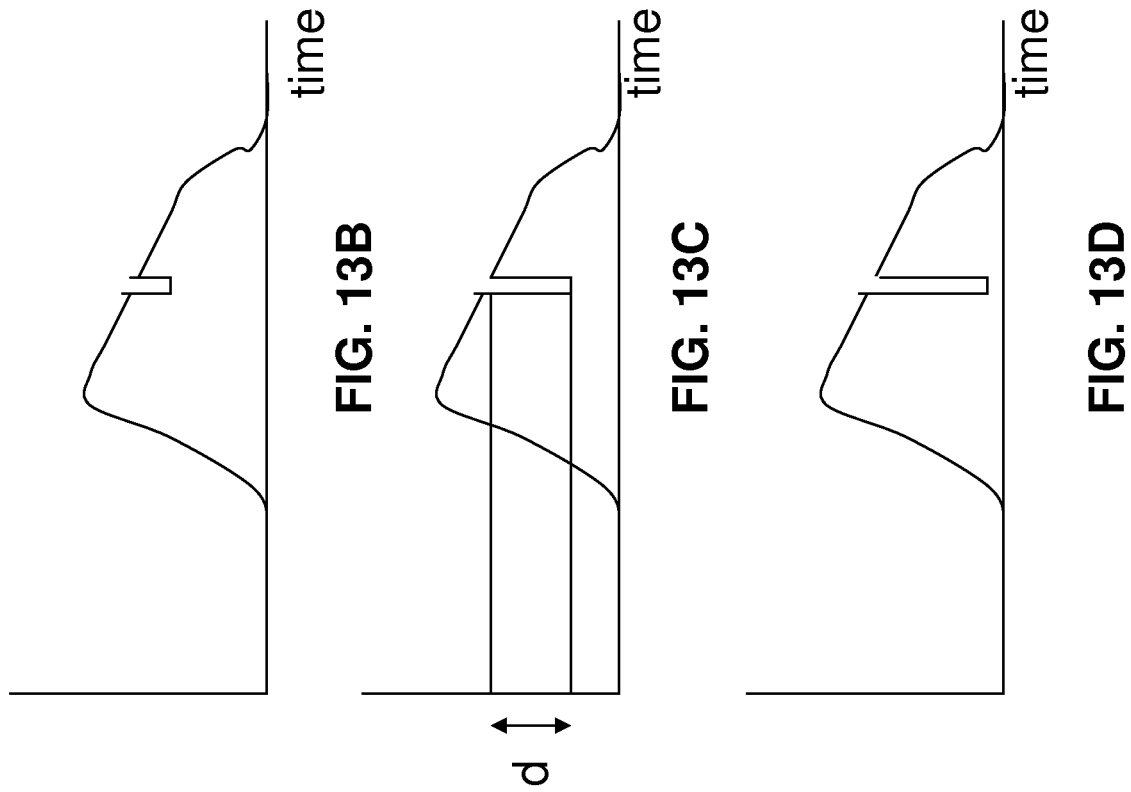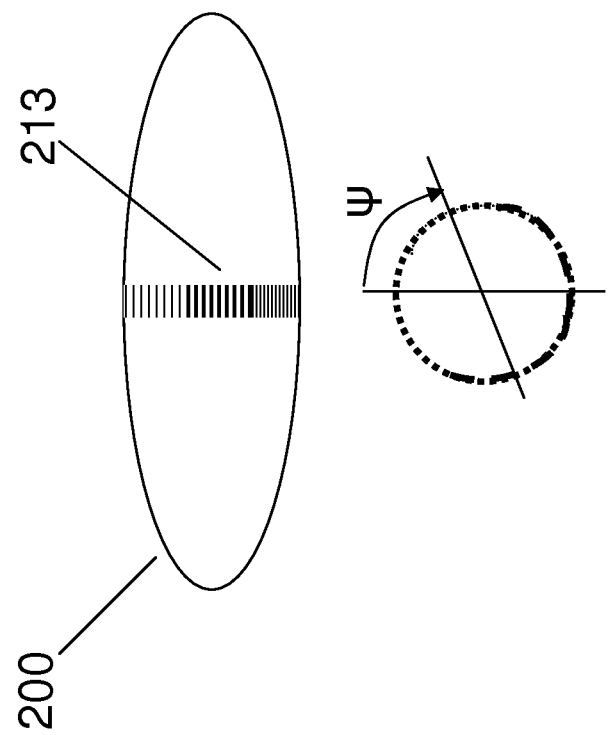

US 9,332,960 B2

SYSTEM AND METHOD FOR DETERMINING LOCATION AND ORIENTATION OF A DEVICE IN-VIVO

CROSS-REFERENCE TO RELATED APPLICATIONS

This application is a National Phase Application of PCT International Application No. PCT/IB2012/000953, International Filing Date Feb. 1, 2012, claiming priority of U.S. Provisional Patent Application No. 61/439,197, filed Feb. 3, 2011, which is hereby incorporated by reference.

TECHNICAL FIELD

The field of determining location of an in-vivo device, and more specifically to determining the in-vivo location and orientation of an in-vivo device, as well as its location and orientation with respect to an external system in which the device is located.

BACKGROUND OF THE INVENTION

Swallowable capsule endoscopes are well-known devices that are used in order to acquire images of in-vivo lumens, e.g., the gastrointestinal (GI) tract. Nowadays, there is an on going need for adding maneuvering capabilities to such capsules and to other in-vivo devices, and thus have the ability to perform various in-vivo operations at specific locations along the lumen that such devices travel along. One method of maneuvering an in-vivo device while in-vivo, is to use external magnetic fields, which may surround the patient being treated by the in-vivo device, and may control the location of the in-vivo device.

The external magnetic fields may also assist in determining location and orientation of the in-vivo device along in-vivo lumens. In order to determine the location and orientation of the device, e.g., a capsule endoscope device, the device may include sensing coils to sense the magnetic fields. The location and orientation of the device may then be calculated based on the strength of the sensed fields. However, such a method requires complex processing to be done inside the in-vivo device. Furthermore, determining location and orientation based on the external magnetic fields, as well as maneuvering the device using the same magnetic fields may create an overload on the external magnetic system.

Therefore, there is a need for a different system and method for determining location (and orientation) of an in-vivo device, e.g., a swallowable capsule, that is not dependent on the same magnetic forces that are used to maneuver the device in-vivo.

SUMMARY

The present invention provides systems and methods for determining location and orientation of an in-vivo device, which is located within an external system applying magnetic fields on the device. In one example, the in-vivo device may be a capsule endoscope imaging as it moves along the GI tract. In other examples, the in-vivo device may be a catheter, an endoscope or any other in-vivo device that may be magnetically maneuvered within a patient's body.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIGS. 13A-13D illustrate a schematic modulation pattern on the housing of the in-vivo device, and captured reflected signals indicating roll angle, in accordance with an embodiment of the present invention.

Figure 1:
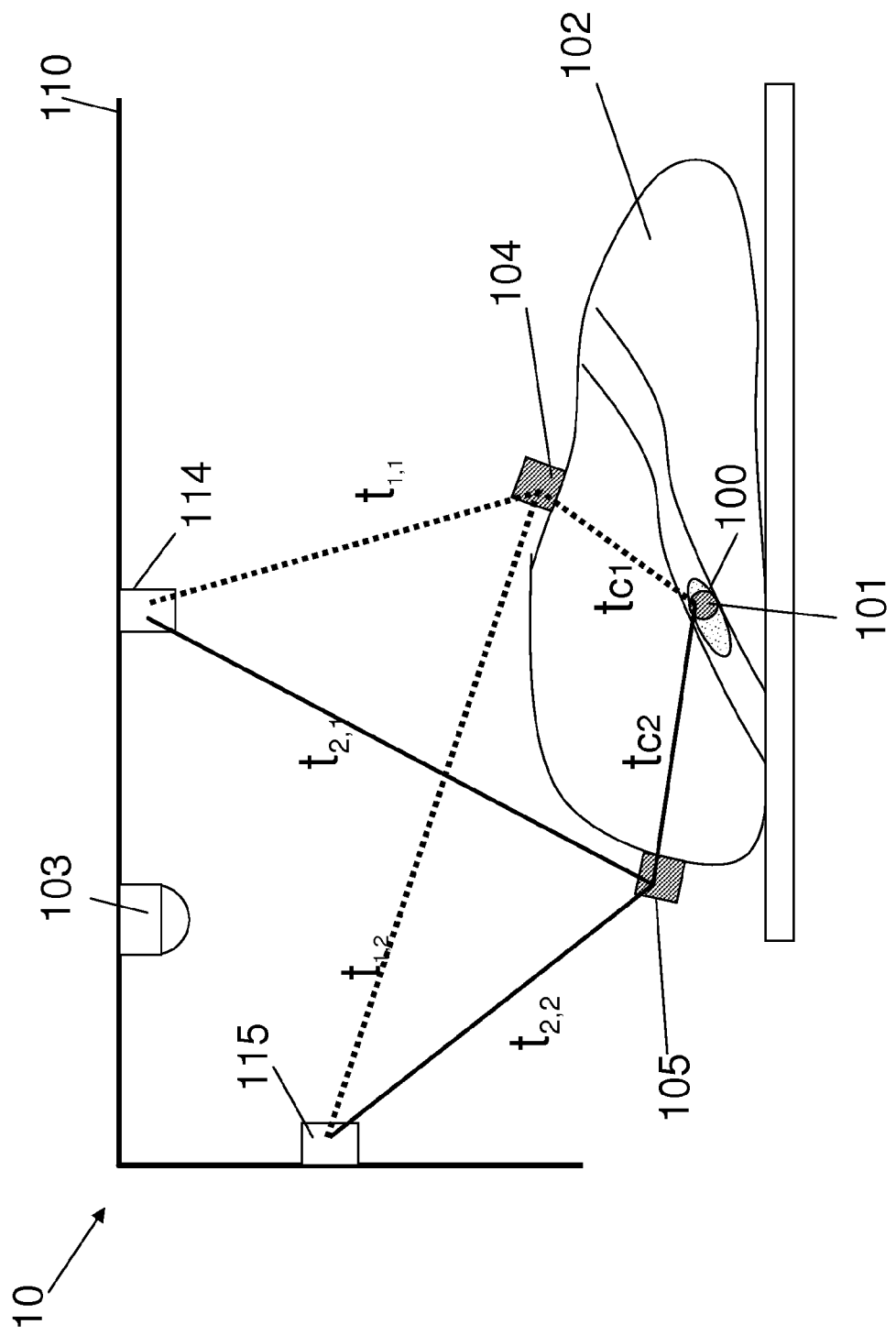
FIG. 1 illustrates a schematic two-dimensional system for determining location of an in-vivo device, in accordance with one embodiment of the present invention.

It will be appreciated that for simplicity and clarity of illustration, elements shown in the figures have not necessarily been drawn to scale. For example, the dimensions of some elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The in-vivo systems and methods described below provide examples of determining location and orientation of in-vivo devices, with respect to the coordinates of the patient's body that the devices are inserted into, and with respect to the coordinates of an external system in which the in-vivo device is located.

Reference is now made to FIG. 1, which illustrates a schematic two-dimensional system 10 for determining location of an in-vivo device, in accordance with an embodiment of the present invention. According to some embodiments, an in-vivo imaging device, e.g., a capsule endoscope 100 may be inserted into a patient's body 102. In some embodiments, the device or capsule 100 may be inserted into the patient 102 through swallowing, ingestion, or it may be inserted into the patient 102 with the assistance of a delivery device. Patient 102 may be placed within a machine frame 110, which may comprise external magnets (not shown) that may be used to maneuver the device 100 by applying magnetic forces on it. In some embodiments, device 100 may comprise an internal magnet, which the external magnets may apply magnetic forces on. In some embodiments, the device 100 may be inserted into the body of the patient 102 before the patient 102 is placed within the machine frame. In other embodiments, the device 100 may be inserted into the patient 102 after the patient is positioned within the frame 110 comprising the external magnets.

In some embodiments, device 100 may comprise an ultrasonic transmitter 101 for transmitting an ultrasonic signal. Ultrasonic transmitter 101 may comprise a small piezoelectric element, such that it may transmit ultrasonic signals to any direction, e.g., ultrasonic transmitter 101 may transmit signals omni-directionally. According to some embodiments, the intensity of the ultrasonic signals transmitted by ultrasonic transmitter 101 is less important than the importance of the signal reaching all directions at substantially the same time. The intensity of the signal should, however, be high enough to enable its detection.

Device 100 may comprise an imaging system, which may comprise an optical system and an imager for acquiring images of the lumen that device 100 passes through. Device 100 may further comprise a transmitter for transmitting the in-vivo acquired images to an external receiver. The acquired images may be displayed on a monitor or screen for the convenience of the operator of the machine frame 110 and the device 100. The images may be displayed in real time, so as to enable the operator of the device 100 to maneuver device 100 according to the acquired images. For example, the operator may determine in-vivo location of device 100 according to real time displayed images, and may then decide on a new location towards which to maneuver the imaging device 100. Device 100 may comprise an internal power source, such as one or more batteries. Yet, in other embodiments, device 100 may only comprise a capacitor that may be supplied with electrical power by an external powering device. In some embodiments, the external magnets may be used to energize device 100.

Device 100 may comprise various tools for performing operations at specific locations along the lumen. For example, device 100 may comprise a chamber into which a biopsy, or sample of in-vivo tissue may be inserted, after being sucked and cut by a blade or any other cutting element that device 100 may further comprise. In some embodiments, the sample may be a fluid sample of in-vivo fluid. Device 100 may comprise an imager for acquiring images of the lumen it passes along, as well as acquiring images of the chamber. In other embodiments, device 100 may comprise separate imagers; one for imaging the in-vivo lumen and one for imaging the chamber. In some embodiments, the device 100 may comprise a medicament that may be injected or released from device 100 at a target location along the lumen.

According to some embodiments, machine frame 110 may comprise a radio beacon transmitter 103 that may transmit a radio pulse. The machine frame 110 may further comprise at least two sonic detectors 114 and 115. According to some embodiments, at least two transponders 104 and 105 may be placed or attached onto the patient's body 102.

In some embodiments, radio beacon transmitter 103 may transmit a radio pulse that may trigger transmission of signals of other components in system 10. The radio signal sent by radio beacon 103 may reach all of the components of system 10 at substantially the same time, thus causing a reaction of signals that have the same start time. According to some embodiments, ultrasonic transmitter 101 in device 100 may be triggered by the radio pulse sent by radio beacon 103. Thus, ultrasonic transmitter 101 may send an ultrasonic signal.

Once radio beacon 103 sends a radio pulse, each of the two transponders 104 and 105 may be triggered to send a first acoustic signal. Each of transponders 104 and 105 may send a second acoustic signal, once triggered by the ultrasonic signal that may be sent by ultrasonic transmitter 101 present in device 100. The sonic detectors 114 and 115 may detect the first and second acoustic signals that may be transmitted by each of transponders 104 and 105.

As shown in FIG. 1, the ultrasonic signal that may be sent by ultrasonic transmitter 101 may by detected by transponder 104 at time $t_{c1}$. The same ultrasonic signal sent by device 100 may be detected by transponder 105 at time $t_{c2}$. As shown in FIG. 1, the second acoustic signal that may be sent by transponder 104 in response to the ultrasonic signal transmitted by device 100, may be detected by sonic detector 114 at time $t_{1,1}$, whereas that same second acoustic signal may be detected by sonic detector 115 at time $t_{1,2}$. The second acoustic signal that may be sent by transponder 105 in response to the ultrasonic signal transmitted by device 100, may be detected by sonic detector 115 at time $t_{2,2}$, whereas it may be detected by sonic detector 114 at time $t_{2,1}$.

According to some embodiments, in order to prevent the radio pulse transmitted by radio beacon transmitter 103, from triggering operation of other devices that may be located nearby the radio beacon 103 or the machine frame 110, the radio pulse may have a wave form that is more complex than a standard pulse. In order for the components of system 10, e.g., transponders 104 and 105, device 100 and sonic detectors 114 and 115, to detect the unique radio pulse (and in response some components may transmit their own signal), such components may comprise an encoder that may recognize the specific radio pulse sent by radio beacon 103.

According to some embodiments, each of the transponders 104 and 105 may comprise a power supply and a radio receiver for receiving the radio pulse sent by radio beacon transmitter 103. Each of the transponders may further comprise an ultrasonic receiver for receiving an ultrasonic signal from device 100, and a transmitter for transmitting a first acoustic signal in response to the radio pulse and for transmitting a second acoustic signal in response to the ultrasonic signal.

In some embodiments, transponder 104 may transmit acoustic signals at a different frequency than the frequency of signals transmitted by transponder 105. The different signals' frequency of the at least two transponders may enable distinction between the origin of an acoustic signal detected by sonic detectors 114 and 115. That is, the different frequency of acoustic signals detected by sonic detectors 114 and 115 may enable a processor to determine whether a detected signal was transmitted by transponder 104 or whether it was transmitted by transponder 105. In other embodiments, each of the transponders 104 and 105 may transmit an acoustic signal comprising a different specific sound. In yet other embodiments, the acoustic signals transmitted by either of the transponders 104 and 105 may comprise a different code that may ease on distinguishing between the origins of detected acoustic signals. In some embodiments, distinction between the transponders 104 and 105 may be done by time multiplexing.

Figure 2A:
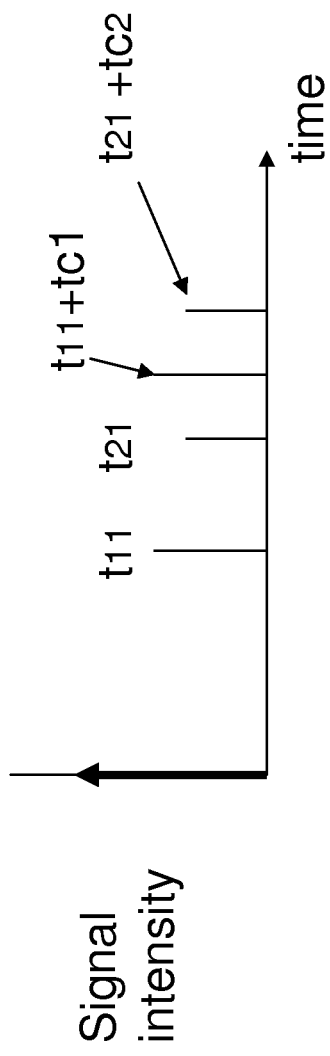
FIGS. 2A-2B illustrate schematic timing diagrams, in accordance with an embodiment of the present invention.
Figure 2B:
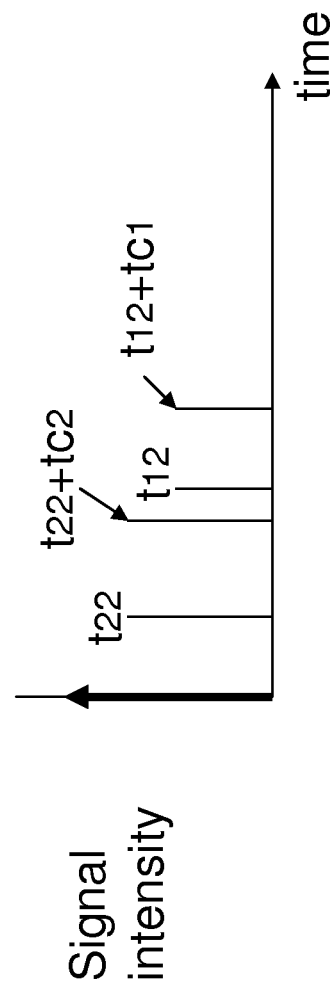

Reference is now made to FIGS. 2A-2B, which illustrate schematic timing diagrams, in accordance with an embodiment of the present invention. FIG. 2A illustrates an example of a timing diagram with respect to sonic detector 114. The diagram in FIG. 2A illustrates the signal density over time per all signals detected by sonic detector 114. For example, the first signal detected by detector 114 may be a signal detected at time $t_{1,1}$ and sent by transponder 104. This signal may have been triggered by the radio pulse transmitted by radio beacon 103, e.g., the signal detected at time $t_{1,1}$ may be the first acoustic signal sent by transponder 104. The second signal that may be detected by detector 114 may have been detected at time $t_{2,1}$. This second signal detected by detector 114 may be the first acoustic signal sent by transponder 105, which may have been triggered by the radio pulse transmitted by radio beacon 103. The third signal that may be detected by detector 114 may be detected at time $t_{1,1}+t_{c1}$. That is, the third detected signal may be one initiated by device 100, and which triggered transponder 104 to send a second acoustic signal. The fourth signal detected by detector 114 may be detected at time $t_{c2}+t_{2,1}$, e.g., this signal may have been initiated by device 100 and may have triggered transponder 105 to send a second acoustic signal.

Similarly, FIG. 2B illustrates an example of a timing diagram with respect to sonic detector 115. The diagram in FIG. 2B illustrates the signal density over time per all signals detected by sonic detector 115. For example, the first signal detected by detector 115 may be a signal detected at time $t_{2,2}$ and sent by transponder 105. This signal may have been triggered by the radio pulse transmitted by radio beacon 103, e.g., the signal detected at time $t_{2,2}$ may be the first acoustic signal sent by transponder 105. The second signal that may be detected by detector 115 may have been detected at time $t_{2,2}+t_{c2}$. This second signal detected by detector 115 may be the second acoustic signal sent by transponder 105, which may have been triggered by an ultrasonic signal transmitted by device 100. The third signal that may be detected by detector 115 may be detected at time $t_{1,2}$. That is, the third detected signal may be first acoustic signal sent by transponder 104 (which may have been triggered by the radio pulse). The fourth signal detected by detector 115 may be detected at time $t_{1,2}+t_{c1}$, e.g., this signal may have been initiated by device 100 and may have triggered transponder 104 to send a second acoustic signal.

Figure 3:
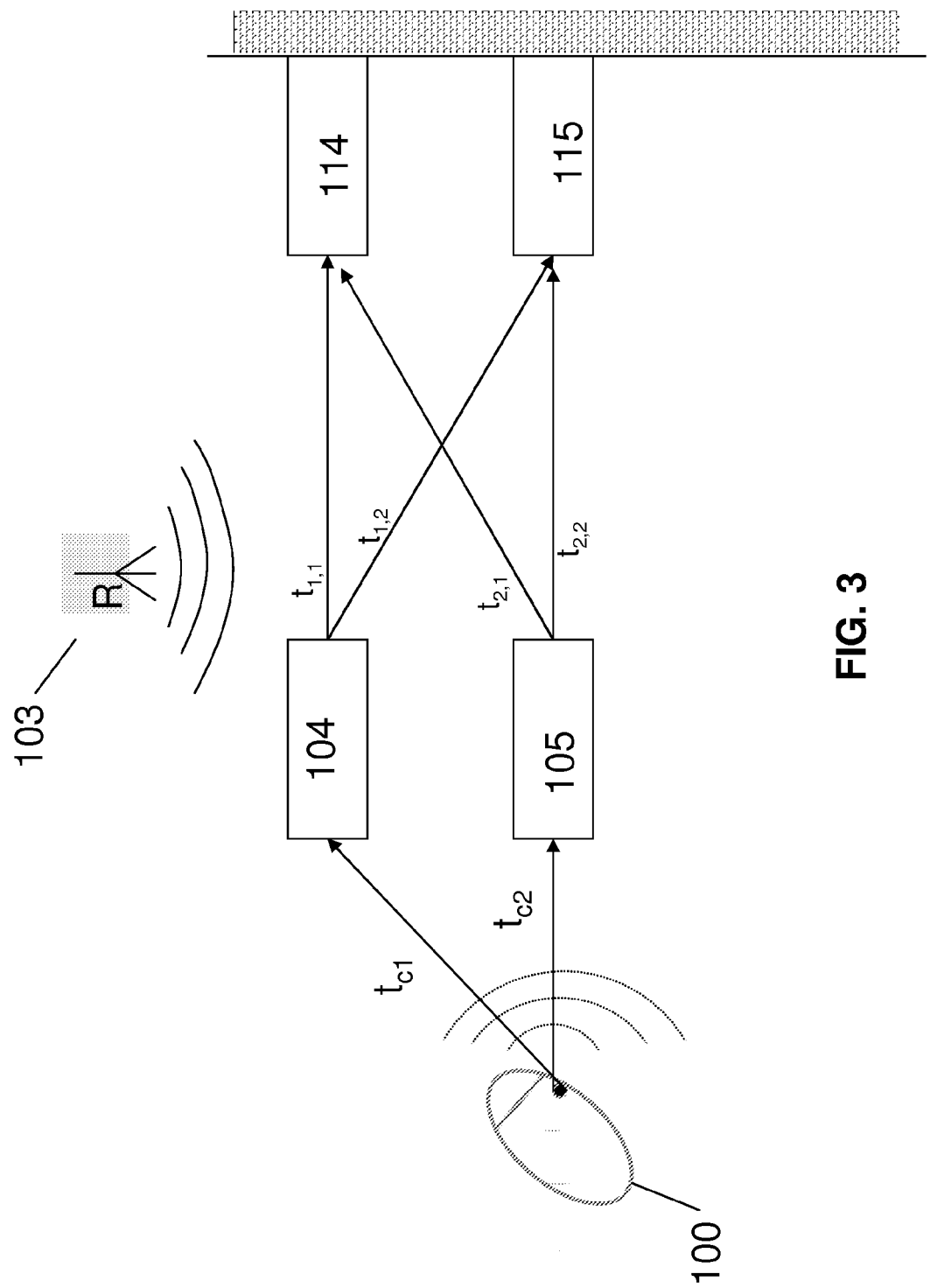
FIG. 3 illustrates a schematic timing connection system, in accordance with an embodiment of the present invention.

Reference is made to FIG. 3, which illustrates a schematic timing connection system, in accordance with an embodiment of the present invention. FIG. 3 illustrates the signal transmission and detection timings that were disclosed with regards to FIG. 1 above, in a more direct manner. According to FIG. 3, the time it may take sonic detector 114 to detect the ultrasonic signal sent by device 100 may be equal to either: $t_{c1}+t_{1,1}$, or to: $t_{c2}+t_{2,1}$. According to FIG. 3, the time it may take sonic detector 115 to detect the ultrasonic signal sent by device 100 may be equal to either: $t_{c2}+t_{2,2}$, or to: $t_{c1}+t_{1,2}$.

The speed of sound in dry air at 20° C. is known to be $V_A$=343.2 [m/sec], thus distance between transponders (104 and 105) and the sonic detectors (114 and 115) may be calculated by the following equation:

Distance[m]=Time[sec]*Speed[m/sec]. (1)

In addition, the speed of sound in the body (or speed of ultrasound in body tissue) is known to be approximately $V_B \approx$1530 [m/sec], thus the distance between the device 100 and any of the transponders (104 and 105) may also be calculated by equation (1).

Figure 4:
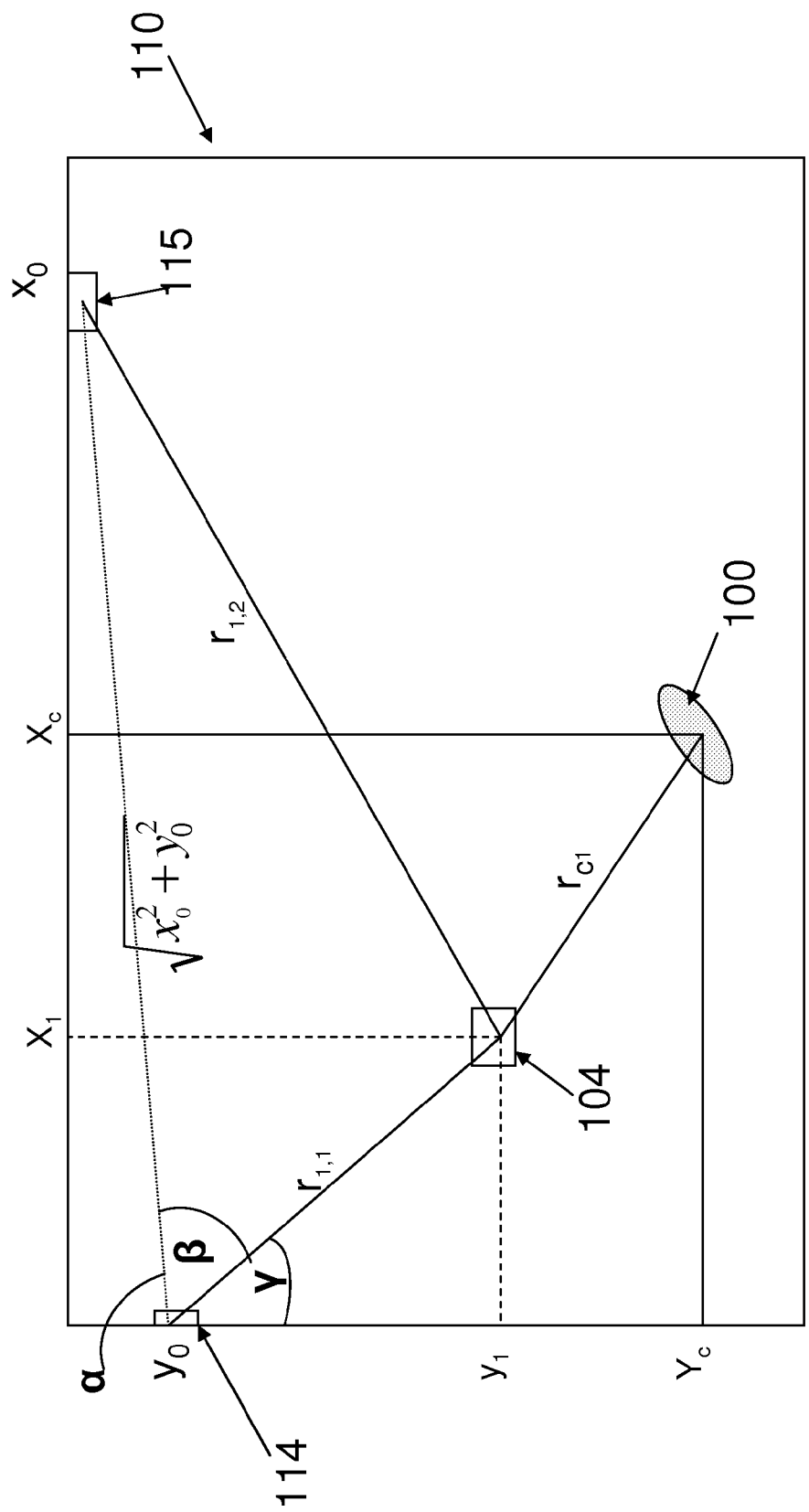
FIG. 4 illustrates a schematic system assisting in calculations of location of an in-vivo device, in accordance with an embodiment of the present invention.

Reference is now made to FIG. 4, which illustrates a schematic system assisting in calculations of location of an in-vivo device, in accordance with an embodiment of the present invention. According to equation (1), if the time it takes a signal to reach any of the sonic detectors 114 and 115 is known, then the distance between the sonic detectors 114 and 115 and the components of system 10 (e.g., transponders 104 and 105 and/or device 100) which sent the signal, may be determined. The following equation may be used in order to calculate the distance between the transponders 104 and 105 and sonic detectors 114 and 115:

$$\begin{bmatrix} t_{1,1} & t_{1,2} \\ t_{2,1} & t_{2,2} \end{bmatrix} \times V_A = \begin{bmatrix} r_{1,1} & r_{1,2} \\ r_{2,1} & r_{2,2} \end{bmatrix} \quad (2)$$

Whereby, $t_{i,j}$ represents the time it takes a signal to reach a sonic detector (j) when transmitted from a transponder (i), and $V_A$ represents the velocity of sound in dry air. The following equation may be used in order to calculate the distance between device 100 and transponders 104 and 105:

$$\begin{bmatrix} t_{c1} \\ t_{c2} \end{bmatrix} \times V_B = \begin{bmatrix} r_{c1} \\ r_{c2} \end{bmatrix} \quad (3)$$

Whereby, $t_{ci}$ represents the time it takes a signal to reach transponder (i) when transmitted from device 100 (for example, device 100 may be an endoscope capsule), and $V_B$ represents the velocity of sound in the body.

FIG. 4 illustrates the coordinates $(x_1, y_1)$ of transponder 104 in the coordinates (X, Y) of machine frame 110. In order to calculate the coordinates $(x_1, y_1)$ of transponder 104 in the machine frame's coordinates, the cosine rule may be used:

$a^2=b^2+c^2-2bc \cos \delta$; Whereby: (4)

Angle β shown in FIG. 4, may be defined between the distance $r_{1,1}$ (i.e., the distance between transponder 104 and sonic detector 114) and $\sqrt{x_0^2+y_0^2}$ (i.e., the distance between sonic detector 114 and sonic detector 115). In order to calculate angle β, equation (4) may be used as follows:

$$\beta = \arccos\left(\frac{x_0^2+y_0^2+r_{1,1}^2-r_{1,2}^2}{2\sqrt{x_0^2+y_0^2} \cdot r_{1,1}}\right) \quad (5)$$

In order to calculate the $(x_1, y_1)$ coordinates of transponder 104 with respect to the machine frame coordinates (X,Y), the following equations may be used:

$y_1=r_{1,1} \cos(\gamma)+y_0$; (6)

$x_1=r_{1,1} \sin(\gamma)$; (7)

Whereby: $\gamma=180°-\alpha-\beta=180°-\arctan(x_0/y_0)-\beta$

Figure 5:
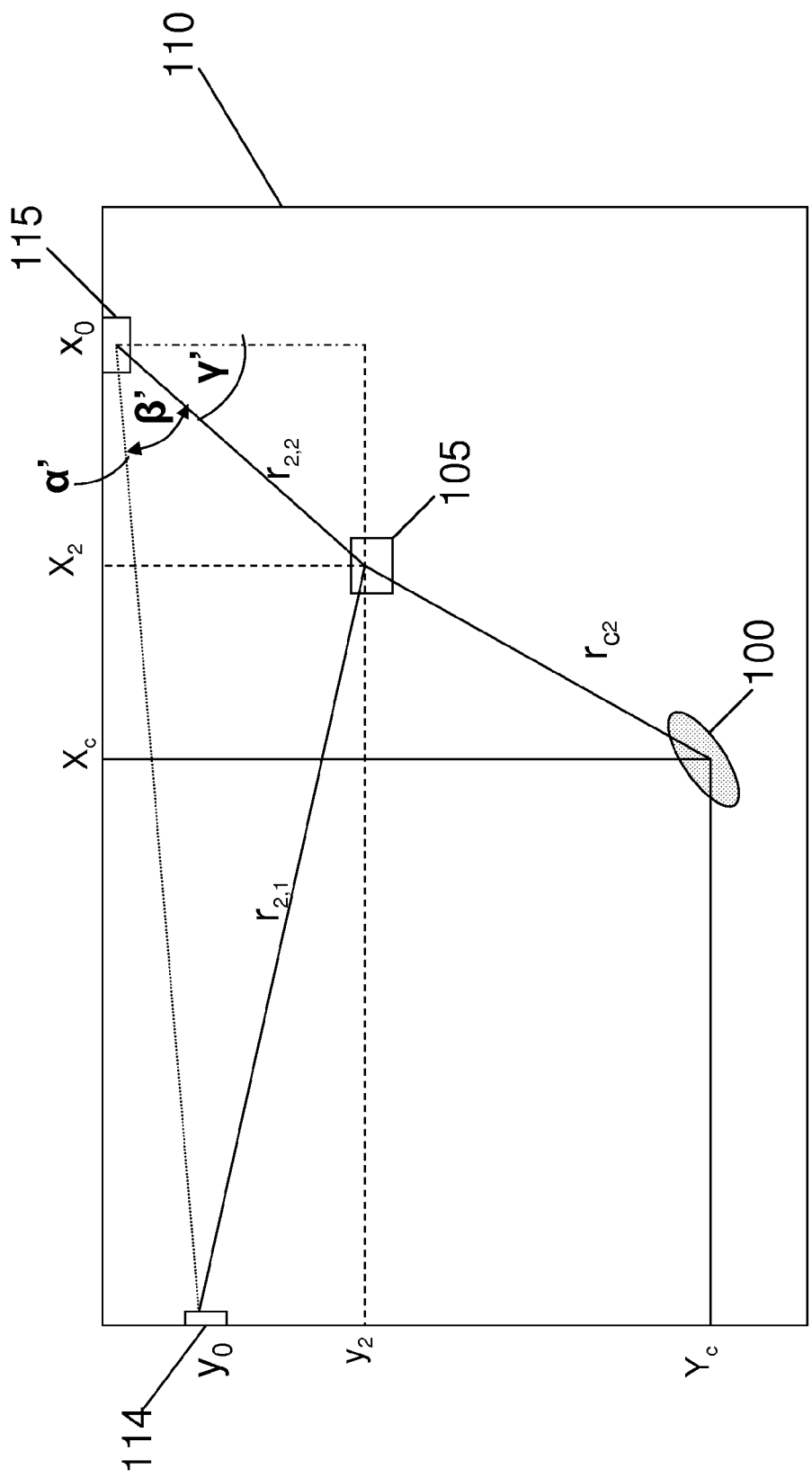
FIG. 5 illustrates a schematic system assisting in calculations of location of an in-vivo device, in accordance with an embodiment of the present invention.

Reference is made to FIG. 5, which illustrates a schematic system assisting in calculations of location of an in-vivo device, in accordance with an embodiment of the present invention. The coordinates $(x_2, y_2)$ of transponder 105 with respect to the coordinates (X,Y) of machine frame 110 may be calculated, following equations (1) to (7) above, with minor adjustments.

Angle β' shown in FIG. 5, may be defined between the distance $r_{2,2}$ (i.e., the distance between transponder 105 and sonic detector 115) and $\sqrt{x_0^2+y_0^2}$ (i.e., the distance between sonic detector 114 and sonic detector 115). In order to calculate angle β', equation (4) may be used as follows:

$$\beta' = \arccos\left(\frac{x_0^2 + y_0^2 + r_{2,2}^2 - r_{2,1}^2}{2\sqrt{x_0^2 + y_0^2} \cdot r_{2,2}}\right) \quad (5')$$

In order to calculate the $(x_2, y_2)$ coordinates of transponder 105 with respect to the machine frame coordinates (X,Y), the following equations may be used:

$$y_2 = r_{2,2} \cos(\gamma') \quad (6')$$

$$x_2 = x_0 - r_{2,2} \sin(\gamma'); \quad (7')$$

Whereby: $\gamma' = 180° - \alpha' - \beta' = 180° - \arctan(x_0/y_0) - \beta'$.

Figure 6:
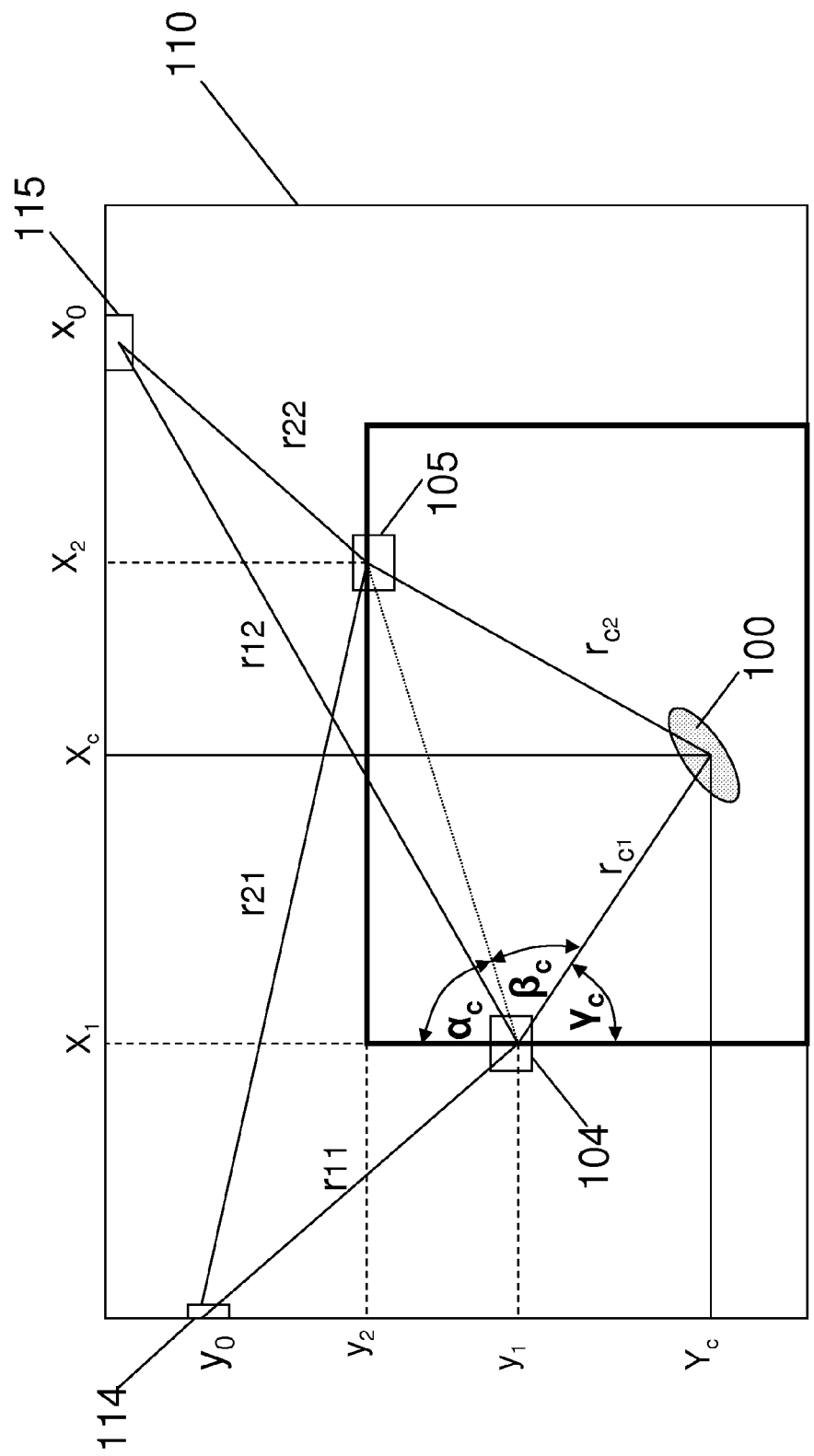
FIG. 6 illustrates a schematic system assisting in calculations of location of an in-vivo device, in accordance with an embodiment of the present invention.

Reference is now made to FIG. 6, which illustrates a schematic system assisting in calculations of location of an in-vivo device, in accordance with an embodiment of the present invention. FIG. 6 illustrates the coordinates $(X_c, Y_c)$ of the device 100 (e.g., capsule endoscope 100) with respect to the coordinates (X,Y) of machine frame 110. The coordinates $(X_c, Y_c)$ of device 100 may be calculated following equations (1) to (7) above, with minor adjustments. Angle $\beta_c$ shown in FIG. 6, may be defined between the distance $r_{c1}$ (i.e., the distance between transponder 104 and device 100) and $\sqrt{(x_2-x_1)^2+(y_1-y_2)^2}$ (i.e., the distance between transponder 104 and transponder 105). In order to calculate angle $\beta_c$, equation (4) may be used as follows:

$$\beta_c = \arccos\left(\frac{(x_2 - x_1)^2 + (y_1 - y_2)^2 + r_{c1}^2 - r_{c2}^2}{2\sqrt{(x_2 - x_1)^2 + (y_1 - y^2)^2} \cdot r_{c1}}\right) \quad (5'')$$

In order to calculate the $(X_c, Y_c)$ coordinates of device 100 with respect to the machine frame coordinates (X,Y), the following equations may be used:

$$Y_c = y_1 + r_{c1} \cos(\gamma_c) \quad (6'')$$

$$X_c = x_1 + r_{c1} \sin(\gamma_c); \quad (7'')$$

Whereby:

$$\gamma_c = 180° - \alpha_c - \beta_c = 180° - \arctan\left(\frac{x_2 - x_1}{y_1 - y_2}\right) - \beta_c;$$

and $(x_1, y_1)$ which are the coordinates of transponder 104 with respect to machine frame coordinates were already calculated above (see FIG. 4).

According to some embodiments, the calculations performed with the assistance of FIG. 6 in order to find the coordinates $(X_c, Y_c)$ of device 100 based on coordinates $(x_1, y_1)$ of transponder 104, may also be done with respect to coordinates $(x_2, y_2)$ of transponder 105. The purpose of calculating the coordinates of device 100 for a second time, may be to decrease the noise in these calculations. Noise in these calculation may appear due to lack of accuracy in calculating the distances between the components of system 10 (e.g., $r_{i,j}$, and $r_{ci}$), which may occur due to lack of accuracy in the measured time it takes a signal to be transmitted from one element of system 10 until it reaches another element of system 10 (e.g., times $t_{i,j}$ and $t_{c1}$).

Figure 7:
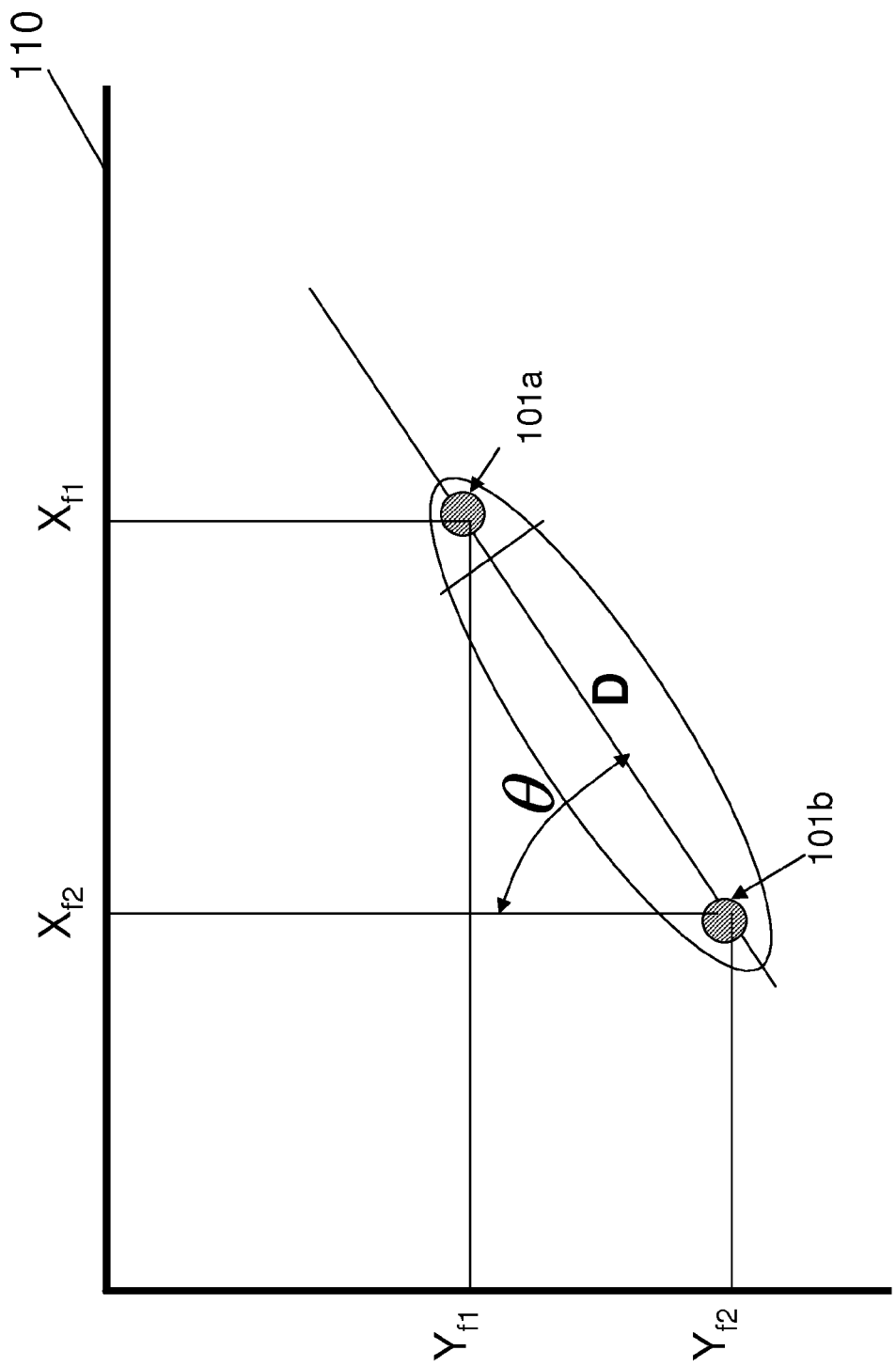
FIG. 7 illustrates a schematic two-dimensional system for determining location and orientation of an in-vivo device, in accordance with one embodiment of the present invention.

Reference is now made to FIG. 7, which illustrates a schematic two-dimensional system for determining location and orientation of an in-vivo device, in accordance with one embodiment of the present invention. In order to determine orientation of in-vivo device 100, which may assist in better understanding which direction the device 100 is heading while passing through the lumen, device 100 may comprise at least two separate ultrasonic transmitters, e.g., ultrasonic transmitters 101a, and 101b. The at least two ultrasonic transmitters (e.g., 101a, 101b) may be located at opposite ends of device 100. Other numbers of ultrasonic transmitters and other locations along the device 100 may be used. The distance (D) between the ultrasonic transmitters 101a and 101b may be pre-determined. Thus, coordinates of any of the ultrasonic transmitters with respect to the coordinates (X,Y) of machine frame 110 may be calculated as described above, with respect to device 100 comprising one ultrasonic transmitter 101.

According to some embodiments, the transmission frequency of ultrasonic transmitters 101a and 101b may be different. Ultrasonic transmitters sending ultrasonic signals at different frequencies may enable distinction between signals that were detected by either of transponders 104 and 105. Distinction between signals transmitted by the ultrasonic transmitters 101a and 101b may enable more accurate calculations of distance between components of system 10, thus may enable more accurate calculations of location and orientation of device 100 with respect to the patient's body 102, and with respect to machine frame 110. For example, the coordinates of ultrasonic transmitter 101a with respect to the coordinates (X,Y) of machine frame 110 may be $(X_{f1}, Y_{f1})$, and the coordinates of ultrasonic transmitter 101b with respect to coordinates of machine frame 110 may be $(X_{f2}, Y_{f2})$. In some embodiments, the angle of orientation θ may be calculated as follows:

$$\theta = \arctan\left(\frac{Y_{f2} - Y_{f1}}{X_{f1} - X_{f2}}\right) \quad (8)$$

According to some embodiments, in order to determine location and orientation of an in-vivo device, such as device 100, in a 3D system, similar calculations as shown above with respect to equations (1) to (7) may be performed with a few adjustments. For example, in order to determine location, e.g. coordinates $(X_C, Y_C, Z_C)$ of device 100 with respect to the coordinates (X,Y,Z) of machine frame 110, there is a need for at least three transponders (instead of a minimum of two transponders) and thus there is a need for at least three associated sonic detectors (instead of a minimum of two detectors). In some embodiments, in a 3D system, there may be two angles associated with orientation (e.g., $\theta_1$, $\theta_2$) of device 100, both of which may be calculated following equations that may be based upon equation (8) that is shown above with regards to a 2D system, e.g., system 10. A processor (not shown) may perform all of the calculations needed for determining location and orientation of device 100. The processor may be located either within device 100, or located externally to device 100 within machine frame 110, or may be located externally to machine frame 110.

Figure 8:
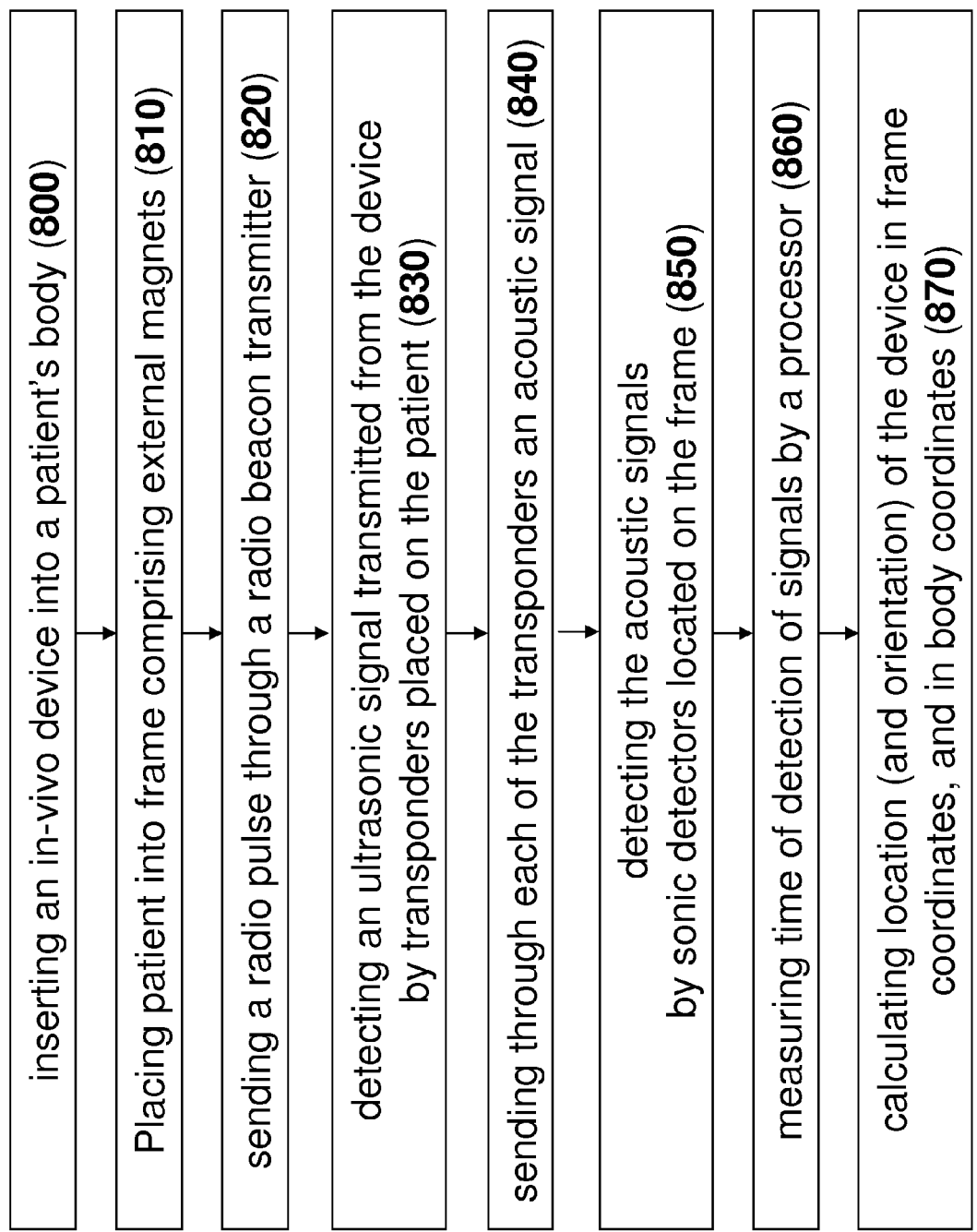
FIG. 8 illustrates a method for determining location of an in-vivo device, in accordance with one embodiment of the present invention.

Reference is now made to FIG. 8, which illustrates a method for determining location of an in-vivo device, in accordance with one embodiment of the present invention. The method may comprise the step of inserting an in-vivo device into a patient's body (800). Inserting an in-vivo device, e.g., device 100, into a patient's body, may be done by swallowing the device or by inserting it with a delivery device (in order to ease on patients that have difficulties in swallowing). The method may further comprise the step of placing the patient into a machine frame comprising external magnets (810). The machine frame, into which the patient is placed, may be similar to machine frame 110 (FIG. 1).

According to some embodiments, the method may comprise the step of sending a radio pulse through a radio beacon transmitter (820). The radio beacon transmitter, e.g., radio beacon 103, may be located on the machine frame, e.g., frame 110. The radio beacon may transmit a radio pulse that may trigger transmission of signals of other components within machine frame 110. Since the speed of radio waves in air is very fast, it may be assumed that the radio pulse reaches all of the components of system 10 substantially simultaneously, thereby determining a start time t=0 for later calculations.

In some embodiments, the method may comprise the step of detecting an ultrasonic signal transmitted from the device (e.g., device 100) by transponders placed on the patient (830). The transponders, e.g., transponders 104 and 105, may be attached to the patient's body for receiving an ultrasonic signal transmitted by an ultrasonic transmitter (e.g., transmitter 101, or transmitters 101*a* and 101*b*). The ultrasonic signal transmitted by the device (e.g., device 100) may be triggered by the radio pulse sent by the radio beacon, e.g., radio beacon 103. The method may further comprise the step of sending through each of the transponders an acoustic signal (840). The transponders (e.g., transponders 104 and 105) may be triggered by the radio pulse to send a first acoustic signal, and may be triggered by the ultrasonic signal to send a second acoustic signal. According to some embodiments, in a 3D system, there should be at least three transponders placed on the patient's body in order to determine location and orientation of an in-vivo device, with respect to the system's coordinates.

The method may further comprise detecting the acoustic signals by sonic detectors located on the frame (850). In a 3D system there should be at least three sonic detectors, in order to determine location and orientation of an in-vivo device with respect to the system's coordinates. The sonic detectors (e.g., sonic detectors 114 and 115) may be attached to the system's frame, e.g., to machine frame 110.

The method may further comprise the step of measuring time of detection of signals by a processor (860). The time it takes each detected signal to reach the sonic detectors may be measured by a processor. The processor may be located within the in-vivo device or it may be external to it, either located within the machine frame or it may be located externally to the machine frame as well.

The method may further comprise the step of calculating location (and orientation) of the device in frame coordinates, and in body coordinates (870). In some embodiments, calculations of the location and orientation of the in-vivo device with respect to the coordinates of the system (e.g., system 10 or machine frame 110) may be performed by the processor. The calculations may be done in accordance with the equations above (e.g., equations (1) to (8)), with adjustments such to conform to 3D systems instead of 2D systems. In some embodiments, in order to determine location of an in-vivo device in a 3D system, the (X,Y,Z) coordinates of the device may be calculated according to equations (1) to (7) with the necessary adjustments from 2D systems to 3D systems. In order to determine orientation of the in-vivo device, the orientation angles (e.g., angle θ) may be calculated according to equation (8) with the necessary adjustments from 2D systems to 3D systems. In some embodiments, in order to determine orientation of an in-vivo device, at least two ultrasonic transmitters should be incorporated into the in-vivo device (e.g., ultrasonic transmitters 101*a* and 101*b*). The angle θ between the at least two ultrasonic transmitters, which is associated with orientation of the device, may be calculated in accordance with equation (8).

Figure 9:
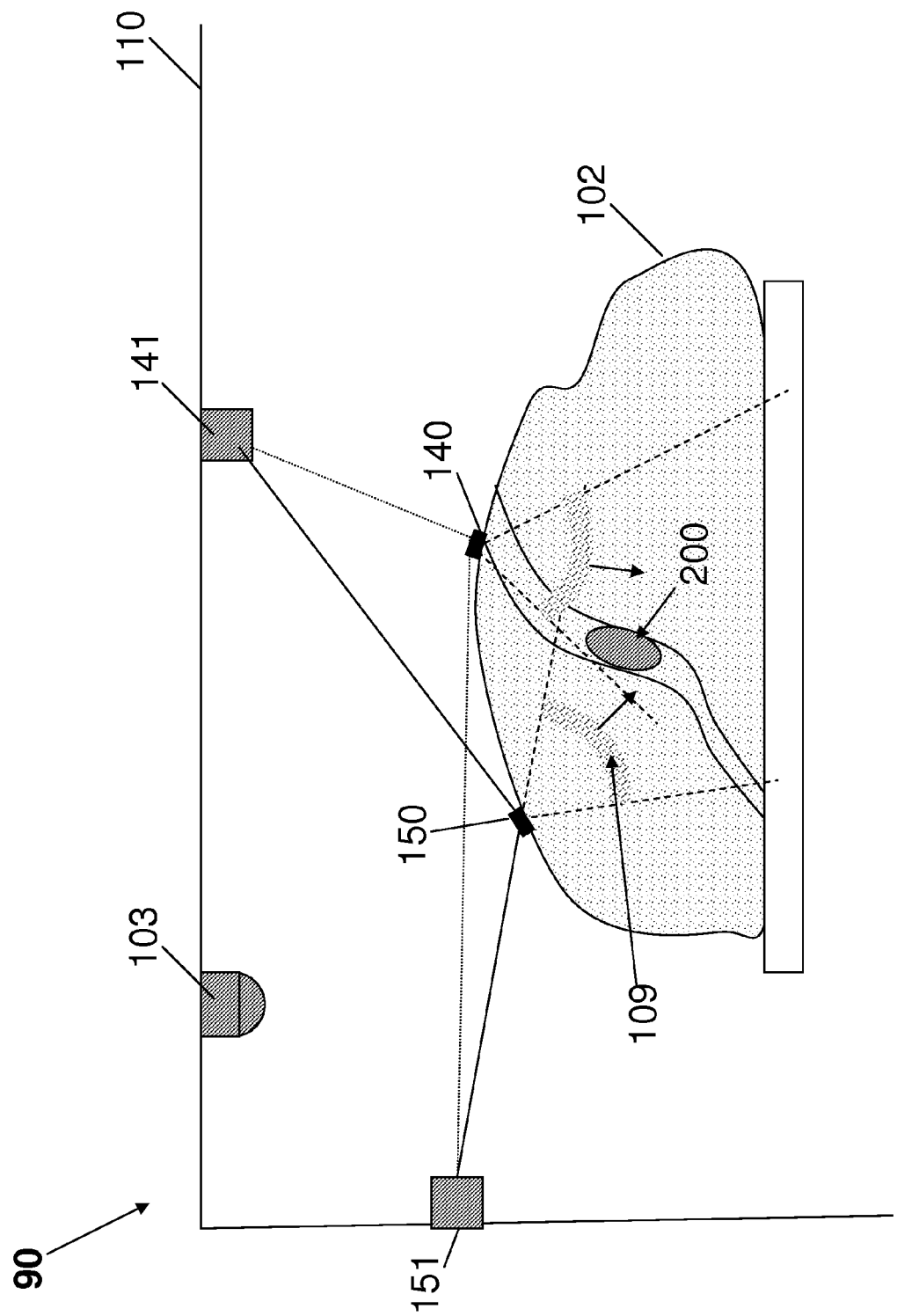
FIG. 9 illustrates a schematic two-dimensional system for determining location of an in-vivo device, in accordance with another embodiment of the present invention.

Reference is now made to FIG. 9, which illustrates a schematic two-dimensional system for determining location of an in-vivo device, in accordance with another embodiment of the present invention. System 90 of FIG. 9 may comprise a machine frame 110, which may comprise external magnets, similarly to the machine frame described in FIG. 1. Patient 102 may be placed within machine frame 110 of system 90. An in-vivo device 200 may be pre-inserted into patient 102 before the patient is placed within machine frame 110. Though, in other embodiments, device 200 may be inserted into patient 102 after the patient 102 is positioned within machine frame 110. Device 200 may comprise a housing that may comprise a proper coating such that device 200 may be a strong reflector. In some embodiments, instead of device 200 comprising an ultrasonic transmitter that may send ultrasonic signals (FIG. 1), the housing of device 200 may act as a reflector, so as to reflect an ultrasonic signal that may be sent towards it. In some embodiments, device 200 may comprise corner reflectors instead of a reflecting coating.

In some embodiments, in a 2D system, patient 102 may have attached at least two transceivers 140 and 150. Transceivers 140 and 150 may send ultrasonic pulses into the body at a wide angle (e.g., an angle that exceeds 90°). In some embodiments, system 90 may further comprise a radio beacon 103 that may send a radio pulse in order to activate the at least two transceivers 140 and 150. 2D system 90 may further comprise at least two sonic detectors 141 and 151.

According to some embodiments, the radio sync pulse (sent by radio beacon 103) may trigger transceivers 140 and 150 to send their corresponding wide angle ultrasonic pulses towards device 200. Simultaneously, the transceivers 140 and 150 may each send a first sonic pulse, which may be received by sonic detectors 141 and 151. When a reflected pulse from device 200 is received by each of the transceivers 140 and 150, a second sonic pulse may be emitted from each of transceivers 140 and 150 towards sonic detectors 141 and 151.

Figure 10A:
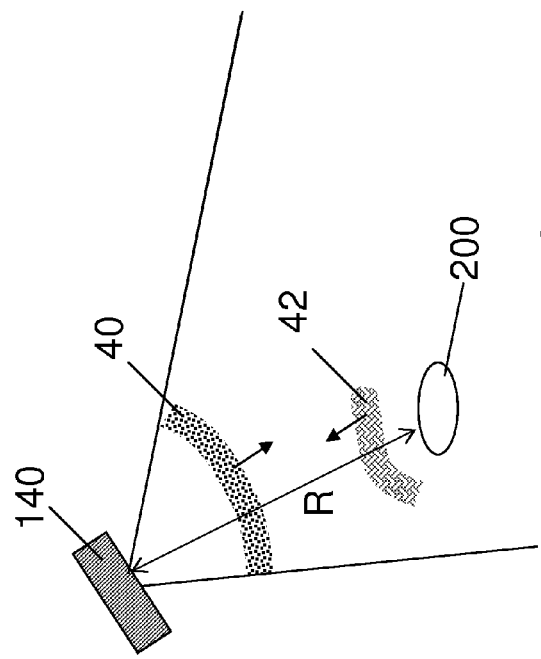
FIGS. 10A-10B illustrate schematic distance estimation between an in-vivo device and a component of the system based on time, in accordance with an embodiment of the present invention.
Figure 10B:
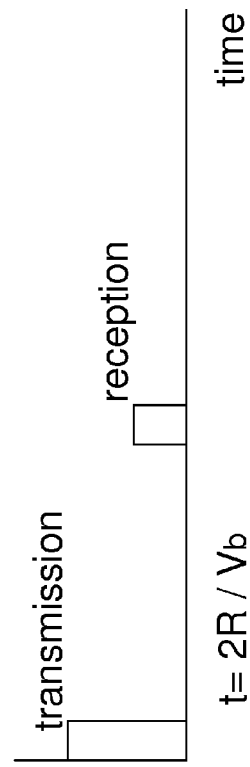

Reference is now made to FIGS. 10A-10B, which illustrate schematic distance estimation between an in-vivo device and a component of the system based on time, in accordance with an embodiment of the present invention. FIG. 10A illustrates transceiver 140 that may send an ultrasonic pulse 40. The ultrasonic pulse 40 may reach device 200. Since device 200 may comprise a reflecting coating, the ultrasonic pulse may be reflected off device 200, thus creating a reflected wave 42, which may be reflected back towards transceiver 140. FIG. 10B illustrates a time diagram that may be used to calculate the distance between the transceiver 140 and device 200. The time it takes an ultrasonic signal to be sent from transceiver 140 to device 200 and then be reflected off device 200 to be received by transceiver 140 may approximately be equal to twice the distance between the transceiver (e.g., transceiver 140) and device 200 divided by the speed of sound in the body. The distance may be calculated based on equation (1) above. Time (t) may be calculated by transceiver 140, and the velocity of sound in the body ($V_B$) is known to be approximately $V_B \approx 1530$ [m/sec], thus distance (R) between the transceiver 140 and device 200 may be: $2R = t*V_B$. The distance R is multiplied by two, since the ultrasonic signal travels from the transceiver and back to it again, so the distance between the transceiver and the device 200 is passed twice by the signal.

According to some embodiments, determining location of the in-vivo device 200 with respect to the coordinates of machine frame 110 may be calculated based on equations (1) to (7) above, with the adjustments of the calculation of distance between device 200 and each of transceivers 140 and 150. In some embodiments, in order to determine location of in-vivo device 200 in a 3D system, adjustments should be made to equations (1) to (7). For example, in a 3D system, the system should comprise at least three transceivers and at least three sonic detectors.

Figure 11B:
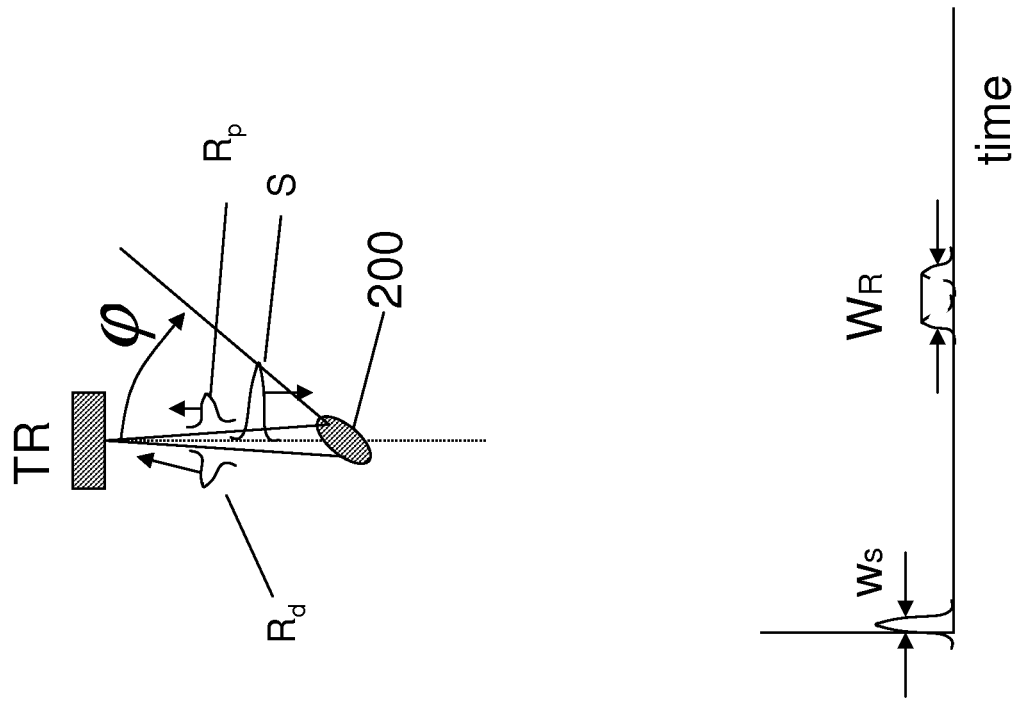
FIGS. 11A-11B illustrate schematic orientation estimations of an in-vivo device based on reflected pulse shape, in accordance with an embodiment of the present invention.
Figure 11A:
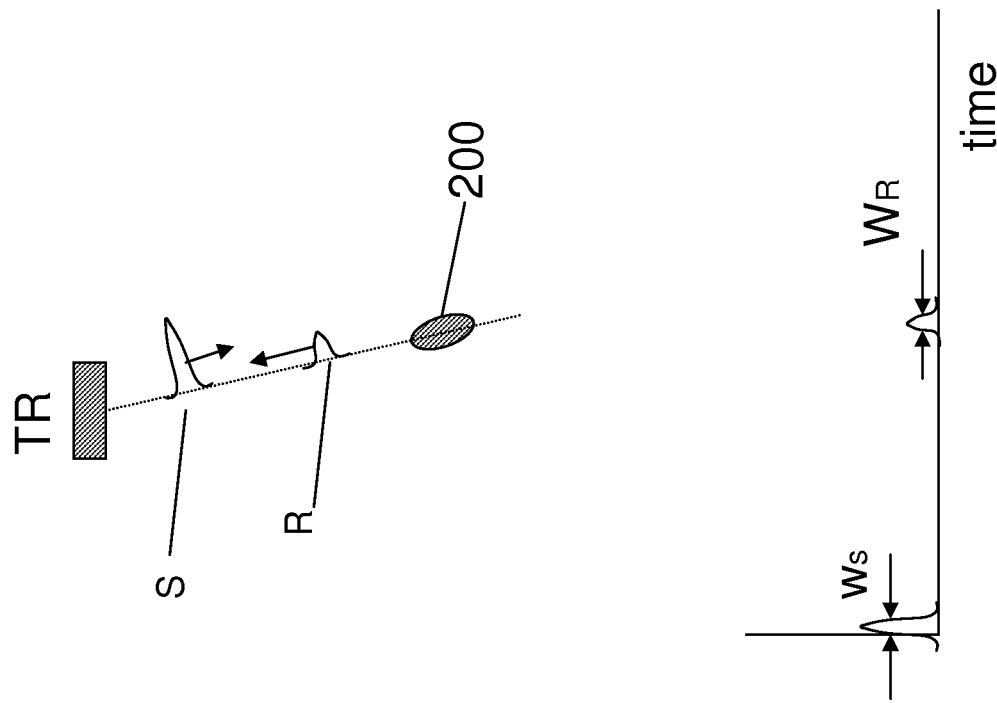

Reference is now made to FIGS. 11A-11B, which illustrate schematic orientation estimations of an in-vivo device based on reflected pulse shape, in accordance with an embodiment of the present invention. FIG. 11A illustrates an example of orientation of device 200, where the longitudinal axis of device 200 intersects with the center of one of the transceivers, e.g., transceiver 140. Since the cross section of device 200 is minimal, the reflected ultrasonic signal (R) (reflected off device 200) may have substantially the same shape as the transmitted signal (S) (transmitted by the transceiver), e.g., the same width: $W_R = W_S$. However, the intensity of the reflected signal is in fact half of the intensity of the transmitted signal.

FIG. 11B illustrates an additional example of orientation of device 200. FIG. 11B illustrates a device 200 tilted with respect to the center of the transceiver (e.g., transceiver 140). Thus, one end of device 200 may be located closer to the transceiver than the other end of device 200. The reflection from the proximal end ($R_p$) may arrive to the transceiver (e.g., transceiver 104) before the reflection from the more distal end ($R_d$) of device 200. Such a difference in time of reflection may result in stretching of the reflected signal, thus the corresponding half intensity width $W_R$ may be wider than the width $W_S$ of the transmitted signal (S). That is, the reflected signal's width may be an indication of the tilt angle (φ) of device 200. The following equation may be used in order to determine the tilt angle (φ):

$$\sin\varphi = \frac{W_R - W_S}{W_{Rmax} - W_S} \quad (10)$$

Therefore, when $W_R = W_S$, then Sin(φ)=0, and tilt angle (φ)=0°. Whereas, when $W_R = W_{Smax}$, then Sin(φ)=1, and tilt angle (φ)=90°. Tilt angles in between the two orientations that are illustrated in FIGS. 11A-B, may be calculated according to the same equation (10).

Figure 12B:
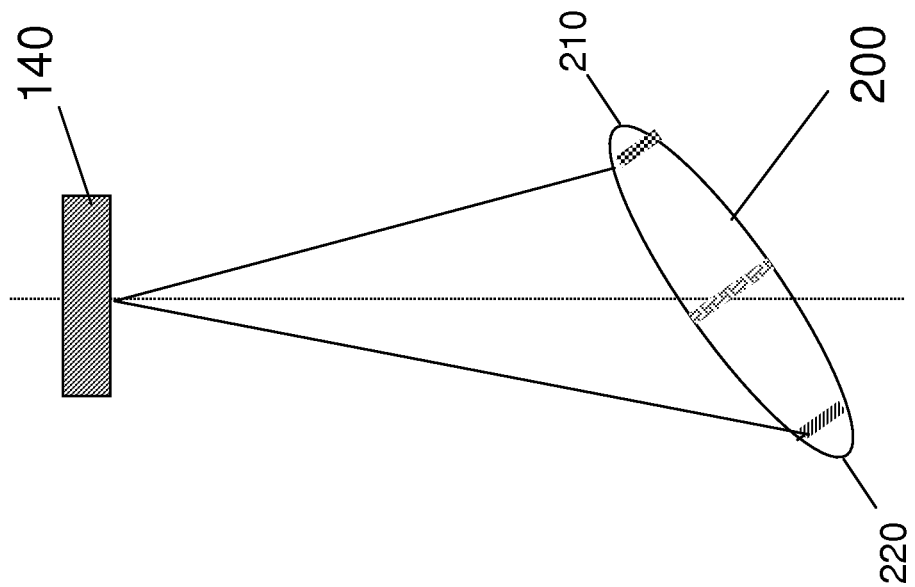
FIGS. 12A-12B illustrate schematic reflection patterns on the in-vivo device, in accordance with an embodiment of the present invention.
Figure 12A:
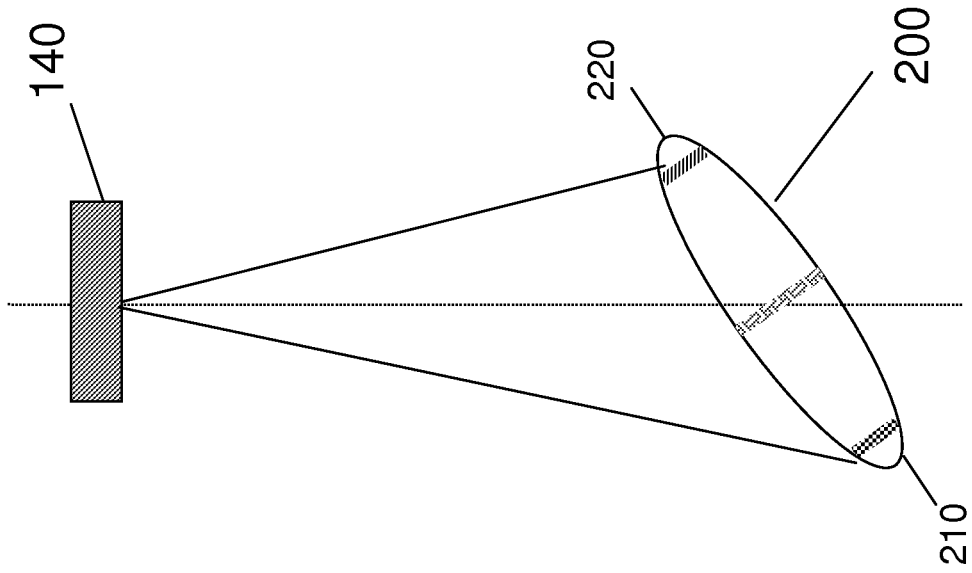

Reference is now made to FIGS. 12A-12B, which illustrate schematic reflection patterns on the in-vivo device, in accordance with an embodiment of the present invention. In some embodiments, device 200 may comprise two imaging systems located at opposite ends of device 200. In other embodiments, device 200 may comprise only one imaging system 210, which may be located at one end of device 200, while the other end 220 does not comprise an imaging system. In embodiments where device 200 may comprise only one imaging system 210, there is a need to distinguish between the ends of device 200, i.e., determine orientation of each of the different ends of device 200, in addition to determining tilt angle (φ) (FIGS. 11A-11B). Therefore, in some embodiments, the housing of device 200 may be designed such to reflect a strong signal (e.g., high intensity) from one end, while reflecting a lower signal from the other end (e.g., low intensity). According to FIG. 12A, if the end 210, which comprises the imaging system, is designed to reflect a stronger signal than end 220, the first reflected signal, which may be received by transceiver 140, may be lower than the second received signal, since end 220 is closer to transceiver 140 than end 210. However, as shown in FIG. 12B, the first reflected signal which may be received by transceiver 140 may be stronger than the second received signal, since in FIG. 12B end 210 is closer to transceiver 140 than end 220.

Reference is now made to FIGS. 13A-13D, which illustrate a schematic modulation pattern on the housing of the in-vivo device, and captured reflected signals indicating roll angle, in accordance with an embodiment of the present invention. According to FIG. 13A, the device 200 may also have a roll angle (ψ), i.e., device 200 may roll around its own longitudinal axis. This may change the orientation of images acquired at different roll angles (ψ). In some acquired images, an object in the image may be located at the top of the image, whereas the same object may be located at the bottom of the acquired image, if the device 200 had rolled around itself between acquisitions of these images. In order to determine roll angle (ψ), the device 200 may be coated in such a way that modulates the reflectivity. In some embodiments, by incorporating a ring 213 of variable reflectivity around the center of the circumference of device 200, a modulation notch may appear at the center of the reflected signal (FIG. 13B). The depth (d) of the notch may be indicative of the roll angle (ψ), as defined by the following equation:

$$\psi = k \cdot d; \text{ wherein } (k) \text{ is a constant.} \quad (11)$$

Accordingly, the roll angle (ψ) may be determined by the depth (d) of the notch. When (d) is relatively small (e.g., FIG. 13B), roll angle (ψ) is also small, e.g., device 200 has just begun to roll. Whereas, when (d) is relatively large (e.g., FIG. 13C, FIG. 13D), roll angle (ψ) is larger than before, e.g., device 200 has rolled in a substantial angle compared to its initial orientation. FIGS. 13A-13D illustrate a reminiscent of radio AM modulation. Other modulations may be used, such as FM modulation.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

The invention claimed is:

1. A system for determining a location of an in-vivo device, the system comprising:
    a frame comprising external magnets and magnetic actuators for surrounding a patient's body, said body comprising an in-vivo device, said in-vivo device comprising an internal magnet, wherein said external magnets are configured for applying magnetic forces on the internal magnet of said in-vivo device;
    a radio beacon transmitter attached to the frame for transmitting a radio pulse;
    wherein said in-vivo device comprises an ultrasonic transmitter for transmitting an ultrasonic signal that is triggered by said radio pulse;
    at least three transponders placed on the patient's body, each transponder sending a first acoustic signal triggered by the radio pulse, and each sending a second acoustic signal triggered by the in-vivo device's ultrasonic signal;

at least three sonic detectors located on the frame for detecting each of the transponders' first and second acoustic signals; and a processor configured for:
measuring a time of detection of said transponders' signals by said sonic detectors,
measuring a time of detection of said in-vivo device's signal by said transponders,
calculating a distance between said transponders and said sonic detectors, based on the time of detection of said transponders' signals,
calculating a distance between the in-vivo device and said transponders, based on the time of detection of the in vivo device's signal, and
determining the location of the in-vivo device in frame coordinates, and in body coordinates, based on both the distance between the transponders and the sonic detectors, and the distance between the in-vivo device and the transponders.

2. The system according to claim 1, wherein each transponder comprises an ultrasonic receiver and a sonic transmitter.

3. The system according to claim 1, wherein said sonic detectors are connected to the processor.

4. The system according to claim 1, wherein said in-vivo device comprises at least two ultrasonic transmitters, each transmitting an ultrasonic signal having a different frequency.

5. The system according to claim 1, wherein said in-vivo device is a swallowable capsule endoscope.

6. The system according to claim 1, wherein said device comprises tools for performing operations at a target location in-vivo.

7. A method for detecting a location of an in-vivo device, the method comprising:
inserting an in-vivo device into a patient's body, said device comprising an ultrasonic transmitter and an internal magnet;
placing the patient into a frame surrounding said patient, the frame comprising external magnets for applying magnetic forces on the internal magnet of the in-vivo device;
sending a radio pulse through a radio beacon transmitter to at least three transponders placed on the patient, and to the in-vivo device, for triggering each of the transponders to transmit an acoustic signal and for triggering the device to transmit an ultrasonic signal at substantially the same time period;
detecting the ultrasonic signal transmitted from the device by said transponders placed on the patient;
sending through each of the transponders an acoustic signal that is triggered by the device's ultrasonic signal;
detecting the acoustic signals sent through each of the transponders by at least three sonic detectors located on the frame;
measuring, by a processor, a time of detection of said transponders' signals by said sonic detectors;
measuring, by said processor, a time of detection of said in-vivo device's signal by said transponders;
calculating, by said processor, a distance between said transponders and said sonic detectors, based on the time of detection of said transponders' signals;
calculating, by said processor, a distance between the in-vivo device and said transponders, based on the time of detection of the in vivo device's signal; and
determining the location of the device in frame coordinates, and in body coordinates, based on both the distance between the transponders and the sonic detectors, and the distance between the in-vivo device and the transponders.

8. The method according to claim 7, wherein said device comprises at least two ultrasonic transmitters each transmitting an ultrasonic signal, and wherein determining the location of the device further comprises determining the location of each of the device's ultrasonic transmitters, thus calculating the in-vivo orientation of the device.

9. The method according to claim 7, wherein said in-vivo device is a swallowable capsule endoscope.

10. A method for detecting a location of an in-vivo device, the method comprising:
inserting an in-vivo device into a patient's body, said device comprising an internal magnet and a coating so as to reflect an ultrasonic signal;
placing the patient into a frame surrounding said patient, the frame comprising external magnets for applying magnetic forces on the internal magnet of the in-vivo device;
sending a radio pulse through a radio beacon transmitter to at least three transponders placed on the patient, for triggering each of the transponders to transmit a first sonic signal and for triggering each of the transponders to send an ultrasonic signal towards the in-vivo device, at substantially the same time period;
detecting a reflected ultrasonic signal reflected off the device, by said transponders placed on the patient;
sending through each of the transponders a second sonic signal, which is triggered by the device's reflected ultrasonic signal;
detecting the first and second sonic signals sent through each of the transponders, by at least three sonic detectors located on the frame;
measuring, by a processor, a time of detection of said transponders' signals by said sonic detectors;
measuring, by said processor, a time of detection of said in-vivo device's signal by said transponders;
calculating, by said processor, a distance between said transponders and said sonic detectors, based on the time of detection of said transponders' signals;
calculating, by said processor, a distance between the in-vivo device and said transponders, based on the time of detection of the in vivo device's signal; and
determining the location of the device in frame coordinates, and in body coordinates, based on both the distance between the transponders and the sonic detectors, and the distance between the in-vivo device and the transponders.

* * * * *